United States Patent [19]

Schirmer et al.

[11] Patent Number: 4,914,128
[45] Date of Patent: Apr. 3, 1990

[54] ACRYLATES AND FUNGICIDES WHICH CONTAIN THESE COMPOUNDS

[75] Inventors: Ulrich Schirmer, Heidelberg; Stefan Karbach, Ludwigshafen; Ernst-Heinrich Pommer, Limburgerhof; Eberhard Ammermann, Ludwigshafen; Wolfgang Steglich, Bonn-Roettgen; Barbara A. M. Schwalge, Lohmar; Timm Anke, Kaiserslautern, all of Fed. Rep. of Germany

[73] Assignee: BASF Aktiengesellschaft, Ludwigshafen, Fed. Rep. of Germany

[21] Appl. No.: 257,129

[22] Filed: Oct. 11, 1988

Related U.S. Application Data

[63] Continuation of Ser. No. 939,109, Dec. 8, 1986, abandoned.

[30] Foreign Application Priority Data

Dec. 20, 1985 [DE] Fed. Rep. of Germany ....... 3545319

[51] Int. Cl.$^4$ .................. A01N 37/12; C07C 69/618
[52] U.S. Cl. ..................................... 514/532; 558/11; 558/13; 558/24; 558/37; 558/46; 558/47; 558/57; 558/58; 560/60; 560/56; 560/53; 560/45; 560/37; 560/34; 560/28; 560/27; 560/21; 560/13; 560/12; 560/11; 560/10
[58] Field of Search ............... 514/532, 544, 542, 541, 514/539, 533, 531, 530; 260/507 R; 558/11, 13, 24, 37, 46, 47, 57, 58; 560/60, 45, 56, 53, 37, 34, 28, 27, 21, 13, 12, 11, 10

[56] References Cited

U.S. PATENT DOCUMENTS

| | | | |
|---|---|---|---|
| 3,468,885 | 9/1968 | Sane et al. | 260/247.2 |
| 4,709,078 | 11/1987 | Schirmer et al. | 560/60 |
| 4,723,034 | 2/1988 | Schirmer et al. | 560/60 |
| 4,782,177 | 11/1988 | Schirmer et al. | 560/60 |

FOREIGN PATENT DOCUMENTS

| | | |
|---|---|---|
| 15502 | 9/1980 | European Pat. Off. . |
| 44448 | 1/1982 | European Pat. Off. . |
| 178826 | 4/1986 | European Pat. Off. . |
| 1173722 | 7/1964 | Fed. Rep. of Germany . |

OTHER PUBLICATIONS

G. Schramm et al., Strobilurin A und B, Antigungische Stoffwechselprodukte aus Strobilurus Tenacellus, (1978), Chem. Ber. III, 2779-2784.

*Primary Examiner*—Nicky Chan
*Attorney, Agent, or Firm*—Oblon, Spivak, McClelland, Maier & Neustadt

[57] ABSTRACT

Acrylates of the general formula

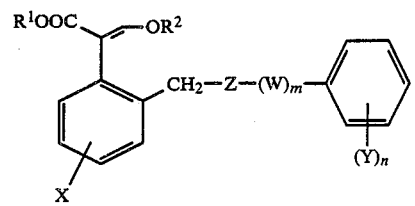

where $R^1$ and $R^2$ independently of one another are each $C_1$–$C_8$-alkyl, X is hydrogen, $C_1$–$C_4$-alkyl, halogen, $C_1$–$C_4$-alkoxy, haloalkyl, cyano or nitro, W is unsubstituted or alkyl-substituted, saturated or unsaturated $C_1$–$C_{10}$-alkylene, Y is hydrogen, alkyl, haloalkyl, alkoxyalkyl, cycloalkyl, aralkyl, aryl, aryloxy, halogen, an unsubstituted or substituted $C_4H_4$ chain which is fused to the benzene radical, alkoxy, haloalkoxy, alkylthio, thiocyanato, cyano, $NO_2$,

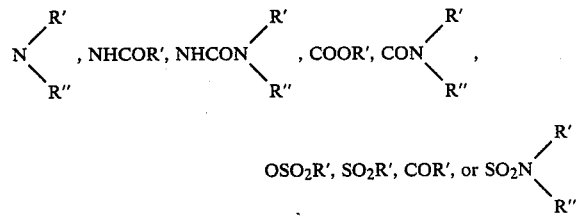

where R' and R" independently of one another are each hydrogen, alkyl, alkoxy, alkylthio or cycloalkyl, or are phenyl which is unsubstituted or substituted by alkyl, halogen or alkoxy, m is 0 or 1, n is from 1 to 4 and Z is oxygen, sulfur, SO or $SO_2$, and fungicides containing them.

5 Claims, No Drawings

ACRYLATES AND FUNGICIDES WHICH CONTAIN THESE COMPOUNDS

This application is a continuation of application Ser. No. 939,109, filed on Dec. 8, 1986, now abandoned.

The present invention relates to novel acrylates and fungicides which contain these compounds.

It has been disclosed that N-tridecyl-2,6-dimethylmorpholine and its salts, e.g. the acetate, can be used as fungicides (DE 11 64 152 and 11 73 722). However, their fungicidal action is unsatisfactory in some cases.

We have found that novel acrylates of the formula

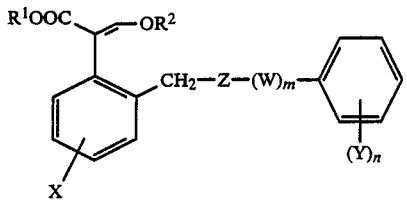

where $R^1$ and $R^2$ independently of one another are each $C_1$-$C_8$-alkyl, X is hydrogen, $C_1$-$C_4$-alkyl, halogen, $C_1$-$C_4$-alkoxy, haloalkyl, cyano or nitro, W is unsubstituted or alkyl-substituted, saturated or unsaturated $C_1$-$C_{10}$-alkylene, Y is hydrogen, alkyl, haloalkyl, alkoxyalkyl, cycloalkyl, aralkyl, aryl, aryloxy, halogen, an unsubstituted or substituted $C_4H_4$ chain which is fused to the benzene radical, alkoxy, haloalkoxy, alkylthio, thiocyanato, cyano, $NO_2$,

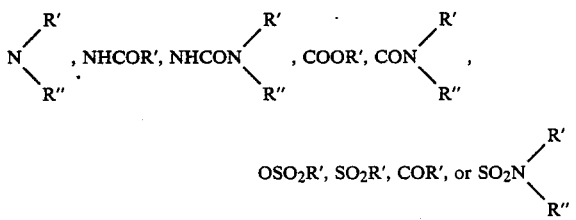

where R' and R" independently of one another are each hydrogen, alkyl, alkoxy, alkylthio or cycloalkyl, or are phenyl which is unsubstituted or substituted by alkyl, halogen or alkoxy, m is 0 or 1, n is from 1 to 4 and Z is oxygen, sulfur, SO or $SO_2$, have an excellent fungicidal action.

The radicals mentioned in the general formula may have, for example, the following meanings: $R^1$ and $R^2$ are each straight-chain or branched $C_1$-$C_8$-alkyl, e.g. methyl, ethyl, isopropyl, n-propyl, n-butyl, sec-butyl, tert-butyl, isobutyl, sec-pentyl, n-hexyl, α-ethyl-n-hexyl or n-octyl), X is hydrogen, $C_1$-$C_4$-alkyl (e.g. methyl or tert-butyl), halogen (e.g. fluorine, chlorine or bromine), $C_1$-$C_4$-alkoxy (e.g. methoxy or n-butoxy), haloalkyl (e.g. trifluoromethyl), cyano or nitro, W is saturated or unsaturated $C_1$-$C_{10}$-alkylene which is unsubstituted or substituted by $C_1$-$C_4$-alkyl (e.g. methylene, methylmethylene, dimethylmethylene, propylene, allylene, hexylene, ethylene, methylethylene, methylpropylene, ethylpropylene, butylene, pentylene, methylpentylene, dimethylpropylene, heptylene, ethylbutylene or trimethylpentylene), Y is hydrogen, $C_1$-$C_{12}$-alkyl (e.g. methyl, ethyl, tert-butyl or dodecyl), haloalkyl (e.g. trifluoromethyl), $C_1$-$C_4$-alkoxy-$C_1$-$C_4$-alkyl (e.g. methoxymethyl), $C_5$-$C_8$-cycloalkyl (e.g. cyclohexyl), aralkyl (e.g. benzyl), aryl (e.g. phenyl), aryloxy (e.g. phenoxy), halogen (e.g. fluorine, chlorine, bromine or iodine), an unsubstituted or substituted $C_4H_4$ chain which is fused to the benzene ring to form an unsubstituted or substituted naphthyl ring, $C_1$-$C_8$-alkoxy (e.g. isopropoxy or hexyloxy), halo-$C_1$-$C_4$-alkoxy (e.g. 1,1,2,2-tetrafluoroethoxy), $C_1$-$C_4$-alkylthio (e.g. methylthio), thiocyanato, cyano, $NO_2$,

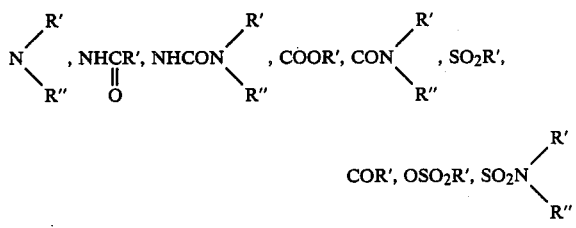

where R' and R" independently of one another are each hydrogen, $C_1$-$C_4$-alkyl (e.g. methyl or ethyl), $C_1$-$C_4$-alkoxy (e.g. methoxy or tert-butoxy), $C_1$-$C_4$-alkylthio (e.g. methylthio) or $C_5$-$C_8$-cycloalkyl (e.g. cyclohexyl), or are each phenyl which is unsubstituted or substituted by $C_1$-$C_4$-alkyl, halogen or $C_1$-$C_4$-alkoxy (e.g. phenyl, 3-chlorophenyl, 4-methylphenyl or 3-methoxyphenyl).

The novel compounds can be prepared, for example, by the following processes: 2-methylphenylacetates of the general formula

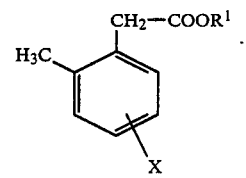

are reacted by the Wislicenus method (Liebigs Annalen 424 (1921), 215 and ibid. 413 (1917), 206) with methyl formate and sodium hydride in an inert solvent. The resulting compounds of the general formula

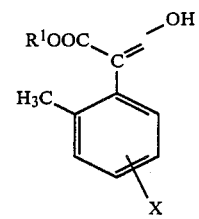

are reacted with an akylating agent in the presence of a base in a solvent (e.g. acetone) to give α-(2-methylphenyl)-β-alkoxyacrylates

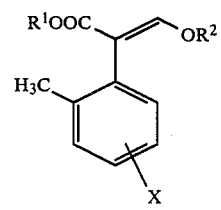

in which $R^1$, $R^2$ and X have the above meanings.

Bromination of this compound with N-bromosuccinimide (Horner and Winkelmann, Angew. Chem. 71

(1959), 349 leads to α-(2-bromomethylphenyl)-β-alkoxyacrylates of the general formula

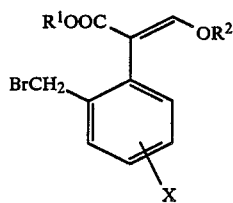

where R¹, R² and X have the above meanings.

The above bromomethyl compounds are reacted with alcohols, phenols or mercaptans to give the novel compounds

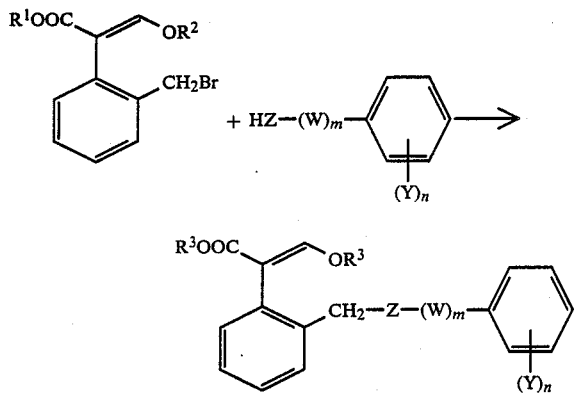

in which R¹, R², X, W, Y, m and n have the above meanings and Z is oxygen or sulfur (cf. Houben-Weyl, Methoden der organischen Chemie VI/3, 54 et seq. (1965)).

The novel compounds in which Z is —SO— or —SO$_2$— are obtained by oxidizing the corresponding —S— compounds:

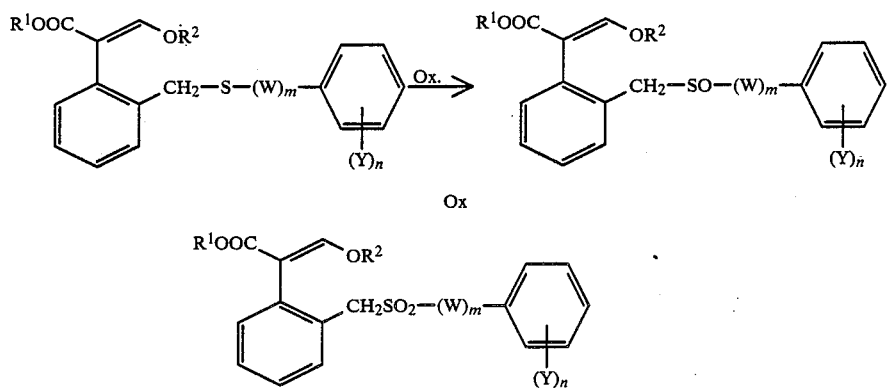

(cf. Houben-Weyl, Methoden der organischen Chemie IX (1955), 213, 228).

The methods below illustrate the synthesis of the starting materials.

METHOD A

Methyl α-(2-methylphenyl)-β-methoxyacrylate 16.5 g of methyl 2-methylphenylacetate are dissolved in 10 ml of methyl formate, and the solution is slowly added dropwise to a suspension of 3 g of sodium hydride in 150 ml of absolute ether. The mixture is refluxed for 4 hours, after which it is acidified with dilute HCl, and the organic phase is separated off, washed with water, dried over MgSO$_4$ and evaporated down to give 13.8 g of a pale yellow oil (methyl α-formyl-(2-methylphenyl)-acetate), which is refluxed with 5.8 ml of dimethyl sulfate, 10.9 g of potassium carbonate and 70 ml of acetone for 1 hour. The mixture is filtered, the filtrate is evaporated down, the residue is taken up in ether, the solution is washed with dilute aqueous ammonia and several times with water, and the ether is stripped off to give 11.3 g of crude methyl α-(2-methylphenyl)-β-methoxyacrylate (bp. 102°–108° C./0.05).

| NMR in CDCl$_3$: | 7.53 | s 1H |
|---|---|---|
| | 7.16–7.36 broad | s 4H |
| | 3.64 | s 3H |
| | 3.73 | s 3H |
| | 2.16 | s 3H |

METHOD B

Methyl α-(2-bromomethylphenyl)-β-methoxyacrylate 20.6 g of the methyl α-(2-methylphenyl)-β-methoxyacrylate obtained as described in Method A, 17.65 g of N-bromosuccinimide, 0.2 g of azobisisobutyronitrile and 150 ml of CCl$_4$ are slowly heated to 90° C. and kept at this temperature until all of the succinimide floats on the solvent. The mixture is filtered, the filtrate is evaporated down, the remaining oil is dissolved in about 5 ml of acetone and the solution is brought to crystallization with n-hexane. 27.5 g of colorless crystals of melting point 86°–87° C. are obtained.

The Examples which follow illustrate the preparation of the novel active ingredients.

EXAMPLE 1

Methyl α-(2-phenoxymethylphenyl)-β-methoxyacrylate 2 g of methyl α-(2-bromomethylphenyl)-β-methoxyacrylate (cf. Method B), 0.65 g of phenol and 1.1 g of potassium carbonate in 20 ml of acetone are refluxed for 24 hours. The mixture is filtered, the filtrate is evaporated down, the residue is taken up in ether, and the solution is extracted twice with sodium carbonate solution and 3 times with water, dried over MgSO$_4$ and evaporated down. The crude product is recrystallized from n-hexane to give 1.7 g of white crystals of melting point 60° C. (compound No. 1).

EXAMPLE 2

Methyl α-(2-[phenylthiomethyl]-phenyl)-β-methoxyacrylate 2 g of methyl α-(2-bromomethylphenyl)-β-methoxyacrylate, 0.65 g of thiophenol and 1.1 g of potassium carbonate are reacted similarly to Example 1. 1.8 g of white crystals of melting point 71° C. are obtained (compound No. 2).

EXAMPLE 3

Methyl α-(2-[phenylsulfoxymethyl]-phenyl)-β-methoxyacrylate 0.6 g of the methyl α-(2-[phenylthiomethyl]-phenyl)-β-methoxyacrylate obtained as described in Example 2 is stirred with 0.39 g of 3-chloroperbenzoic acid in 40 ml of toluene for 5 hours at room temperature. Thereafter, 50 ml of ethyl acetate are added and the mixture is extracted twice by shaking with sodium bicarbonate solution and twice by shaking with water. The organic phase is dried over MgSO$_4$ and evaporated down, and the residue is recrystallized from an ether/n-hexane mixture. 0.56 g of a product of melting point 88° C. is obtained (compound No. 3).

EXAMPLE 4

Methyl α-(2-[phenylsulfonylmethyl]-phenyl)-β-methoxyacrylate 1 g of the methyl α-(2-[phenylthiomethyl]-phenyl)-β-methoxyacrylate obtained as described in Example 2 is reacted with 1.4 g of 3-chloroperbenzoic acid in 40 ml of toluene for 3 days at room temperature similarly to Example 3. 1.0 g of a product of melting point 135° C. (decomposition) is obtained (compound No. 4).

The following compounds can be prepared in a similar manner:

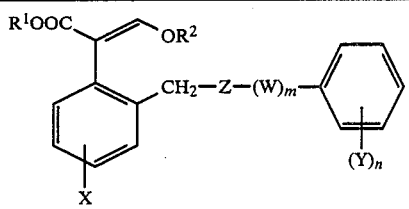

| No. | R$^1$ | R$^2$ | X | Z | W$_m$ | (Y)$_n$ | M.p. °C./NMR |
|-----|-----|-----|---|-----|-------|-------|------|
| 1 | CH$_3$ | CH$_3$ | H | O | — | H | 60° |
| 2 | CH$_3$ | CH$_3$ | H | S | — | H | 71° |
| 3 | CH$_3$ | CH$_3$ | H | SO | — | H | 88° |
| 4 | CH$_3$ | CH$_3$ | H | SO$_2$ | — | H | 135° (decomp.) |
| 5 | CH$_3$ | CH$_3$ | H | O | —CH$_2$— | H | |
| 6 | CH$_3$ | CH$_3$ | H | O | —CH$_2$—CH$_2$— | H | |
| 7 | CH$_3$ | CH$_3$ | H | O | —CH$_2$—CH$_2$—CH$_2$— | H | |
| 8 | CH$_3$ | CH$_3$ | H | O | —CH$_2$—CH=CH— | H | |
| 9 | CH$_3$ | CH$_3$ | H | O | —(CH$_2$)$_5$— | H | |
| 10 | CH$_3$ | CH$_3$ | H | O | —(CH$_2$)$_7$— | H | |
| 11 | CH$_3$ | CH$_3$ | H | O | —(CH$_2$)$_{10}$— | H | |
| 12 | CH$_3$ | CH$_3$ | H | O | —CH$_2$—CH(CH$_3$)— | H | |
| 13 | CH$_3$ | CH$_3$ | H | O | —CH$_2$—CH(CH$_3$)CH$_2$— | H | |
| 14 | CH$_3$ | CH$_3$ | H | O | —CH(CH$_3$)CH$_2$— | H | |
| 15 | CH$_3$ | CH$_3$ | H | S | —CH$_2$— | H | |
| 16 | CH$_3$ | CH$_3$ | H | O | —CH$_2$C≡C— | H | |
| 17 | CH$_3$ | CH$_3$ | H | SO | —CH$_2$— | H | |
| 18 | CH$_3$ | CH$_3$ | H | SO$_2$ | —CH$_2$— | H | |
| 19 | CH$_3$ | CH$_3$ | H | O | —CH$_2$— | 4-Cl | |
| 20 | CH$_3$ | CH$_3$ | H | O | —CH$_2$— | 2,4-Cl$_2$ | |
| 21 | CH$_3$ | CH$_3$ | H | O | —CH$_2$— | 4-CH$_3$ | |
| 22 | CH$_3$ | CH$_3$ | H | O | —CH$_2$— | 3-CH$_3$ | |
| 23 | CH$_3$ | CH$_3$ | H | O | —CH$_2$—CH$_2$— | 4-Cl | |
| 24 | CH$_3$ | CH$_3$ | H | O | —CH$_2$— | 3-CF$_3$ | |
| 25 | CH$_3$ | CH$_3$ | H | O | —CH$_2$— | 4-F | |
| 26 | CH$_3$ | CH$_3$ | H | O | — | 2-Cl | |
| 27 | CH$_3$ | CH$_3$ | H | O | — | 2,4-Cl$_2$ | |
| 28 | CH$_3$ | CH$_3$ | H | O | — | 3-Cl | |
| 29 | CH$_3$ | CH$_3$ | H | O | — | 3,4-Cl$_2$ | |
| 30 | CH$_3$ | CH$_3$ | H | O | — | 4-Cl | |
| 31 | CH$_3$ | CH$_3$ | H | O | — | 3,5-Cl$_2$ | |
| 32 | CH$_3$ | CH$_3$ | H | O | — | 2,4,5-Cl$_3$ | |
| 33 | CH$_3$ | CH$_3$ | H | O | — | 4-Br | |
| 34 | CH$_3$ | CH$_3$ | H | O | — | 4-F | |
| 35 | CH$_3$ | CH$_3$ | H | O | — | 4-OCH$_3$ | |
| 36 | CH$_3$ | CH$_3$ | H | O | — | 4-O-n(C$_4$H$_9$) | |
| 37 | CH$_3$ | CH$_3$ | H | O | — | 4-O-t(C$_4$H$_9$) | |
| 38 | CH$_3$ | CH$_3$ | H | O | — | 4-CH$_3$ | |
| 39 | CH$_3$ | CH$_3$ | H | O | — | 2-CH$_3$ | |
| 40 | CH$_3$ | CH$_3$ | H | O | — | 3-CH$_3$ | |
| 41 | CH$_3$ | CH$_3$ | H | O | — | 4-t-C$_4$H$_9$ | |
| 42 | CH$_3$ | CH$_3$ | H | O | — | 4-cyclo-C$_6$H$_{11}$ | |
| 43 | CH$_3$ | CH$_3$ | H | O | — | 3-benzyl | |
| 44 | CH$_3$ | CH$_3$ | H | O | — | 3-phenoxy | |
| 45 | CH$_3$ | CH$_3$ | H | O | — | 4-phenoxy | |
| 46 | CH$_3$ | CH$_3$ | H | O | — | 3-CH$_2$OCH$_3$ | |

-continued

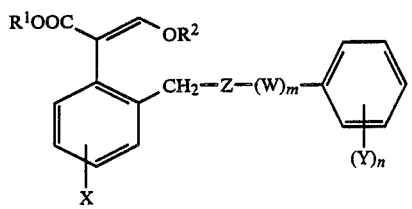

| No. | R¹ | R² | X | Z | W$_m$ | (Y)$_n$ | M.p. °C./NMR |
|---|---|---|---|---|---|---|---|
| 47 | CH₃ | CH₃ | H | O | — | 2-CH₂OCH₃ | |
| 48 | CH₃ | CH₃ | H | O | — | 3-CF₃ | |
| 49 | CH₃ | CH₃ | H | O | — | 4-CF₃ | |
| 50 | CH₃ | CH₃ | H | O | — | 3-C₂H₅ | |
| 51 | CH₃ | CH₃ | H | O | — | 2-OCH₃ | |
| 52 | CH₃ | CH₃ | H | O | — | 3-OCH₃ | |
| 53 | CH₃ | CH₃ | H | O | — | 4-I | |
| 54 | CH₃ | CH₃ | H | O | — | 3-F | |
| 55 | CH₃ | CH₃ | H | O | — | 3,4 (fused ring) | |
| 56 | CH₃ | CH₃ | H | O | — | 2,3 (fused ring) | |
| 57 | CH₃ | CH₃ | H | O | — | 4-OCHF₂ | |
| 58 | CH₃ | CH₃ | H | O | — | 3-OCF₂CHF₂ | |
| 59 | CH₃ | CH₃ | H | O | — | 4-SCH₃ | |
| 60 | CH₃ | CH₃ | H | O | — | 4-CN | |
| 61 | CH₃ | CH₃ | H | O | — | 3-CN | |
| 62 | CH₃ | CH₃ | H | O | — | 4-SCN | |
| 63 | CH₃ | CH₃ | H | O | — | 4-N(CH₃)₂ | |
| 64 | CH₃ | CH₃ | H | O | — | 3-NHCOCH₃ | |
| 65 | CH₃ | CH₃ | H | O | — | 3-NHCOOCH₃ | |
| 66 | CH₃ | CH₃ | H | O | — | 3-NHCON(CH₃)₂ | |
| 67 | CH₃ | CH₃ | H | O | — | 4-COOCH₃ | |
| 68 | CH₃ | CH₃ | H | O | — | 4-CONHCH₃ | |
| 69 | CH₃ | CH₃ | H | O | — | 4-CON(CH₃)₂ | |
| 70 | CH₃ | CH₃ | H | O | — | 4-SO₂CH₃ | |
| 71 | CH₃ | CH₃ | H | O | — | 4-phenylsulfonyl | |
| 72 | CH₃ | CH₃ | H | O | — | 3-COCH₃ | |
| 73 | CH₃ | CH₃ | H | O | — | 4-OSO₂CH₃ | |
| 74 | CH₃ | CH₃ | H | O | — | 4-SO₂N(CH₃)₂ | |
| 75 | CH₃ | CH₃ | H | O | — | 4-CONH-(3-Cl-phenyl) | |
| 76 | CH₃ | CH₃ | H | O | — | 4-benzoyl | |
| 77 | C₂H₅ | CH₃ | H | O | — | H | |
| 78 | i-C₃H₇ | CH₃ | H | O | — | H | |
| 79 | n-C₆H₁₃ | CH₃ | H | O | — | H | |
| 80 | n-C₄H₉ | CH₃ | H | O | — | H | |
| 81 | n-C₃H₇ | CH₃ | H | O | — | H | |
| 82 | s-C₄H₉ | CH₃ | H | O | — | H | |
| 83 | CH₃ | C₂H₅ | H | O | — | H | |
| 84 | CH₃ | i-C₃H₇ | H | O | — | H | |
| 85 | CH₃ | n-C₆H₁₃ | H | O | — | H | |
| 86 | CH₃ | n-C₃H₇ | H | O | — | H | |
| 87 | CH₃ | s-C₄H₉ | H | O | — | H | |
| 88 | CH₃ | CH₃ | 3-CH₃ | O | — | H | |
| 89 | CH₃ | CH₃ | 4-CH₃ | O | — | H | |
| 90 | CH₃ | CH₃ | 5-Cl | O | — | H | |
| 91 | CH₃ | CH₃ | 5-Br | O | — | H | |
| 92 | CH₃ | CH₃ | 6-Cl | O | — | H | |
| 93 | CH₃ | CH₃ | 6-CH₃ | O | — | H | |
| 94 | CH₃ | CH₃ | 5-F | O | — | H | |
| 95 | CH₃ | CH₃ | 5-CF₃ | O | — | H | |
| 96 | CH₃ | CH₃ | H | S | — | 4-Cl | |
| 97 | CH₃ | CH₃ | H | SO | — | 4-Cl | |

-continued

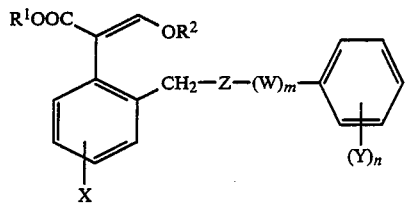

| No. | R¹ | R² | X | Z | W$_m$ | (Y)$_n$ | M.p. °C./NMR |
|---|---|---|---|---|---|---|---|
| 98 | CH₃ | CH₃ | H | SO₂ | — | 4-Cl | |
| 99 | CH₃ | CH₃ | H | S | — | 3-CH₃ | |
| 100 | CH₃ | CH₃ | H | S | — | 4-CH₃ | |
| 101 | CH₃ | CH₃ | H | S | — | 2-CH₃ | |
| 102 | CH₃ | CH₃ | H | S | — | 2,4-Cl₂ | |
| 103 | CH₃ | CH₃ | H | O | — | 4NO₂ | |
| 104 | CH₃ | CH₃ | H | O | — | 2Cl,6F | |
| 105 | CH₃ | CH₃ | H | O | — | 2,3,6(Cl)₃ | |
| 106 | CH₃ | CH₃ | H | O | — | 3,4(CH₃)₂ | |
| 107 | CH₃ | CH₃ | H | O | — | 2-CH₃,4t-C₄H₉ | |
| 108 | CH₃ | CH₃ | H | O | — | 2,4(CH₃)₂ | |
| 109 | CH₃ | CH₃ | H | O | — | 2-NO₂ | |
| 110 | CH₃ | CH₃ | H | O | — | 4-C₁₂H₂₅ | |
| 111 | CH₃ | CH₃ | H | O | — | 4-C₂H₅ | |
| 112 | CH₃ | CH₃ | H | O | — | 3,4,5(OCH₃)₃ | |
| 113 | CH₃ | CH₃ | H | O | — | 2,5(CH₃)₂ | |
| 114 | CH₃ | CH₃ | H | O | — | 2-F | |
| 115 | CH₃ | CH₃ | H | O | — | 2CN | |
| 116 | CH₃ | CH₃ | H | O | — | 2,6-Cl₂ | |
| 117 | CH₃ | CH₃ | H | O | — | 2-Cl,6CN | |
| 118 | CH₃ | CH₃ | H | O | — | 2-Cl,4NO₂ | |
| 119 | CH₃ | CH₃ | H | O | — | 2,4(NO₂)₂ | |

In general terms, the novel compounds are very effective against a broad spectrum of phytopathogenic fungi, in particular those from the class consisting of the Ascomycetes, Phycomycetes and Basidiomycetes. Some of them have a systemic action and can be used as foliar and soil fungicides.

The fungicidal compounds are of particular interest for controlling a large number of fungi in various crops or their seeds, in particular wheat, rye, barley, oats, rice, corn, cotton, soybean, coffee, sugar cane, fruit and ornamentals in horticulture, in viticulture, and for vegetables, such as cucumbers, beans and Cucurbitaceae.

The novel compounds are particularly useful for controlling the following plant diseases:

Erysiphe graminis in cereals,
Erysiphe cichoracearum and Sphaerotheca fuliginea in Cucurbitaceae,
Podosphaera leucotricha in apples,
Uncinula necator in vines,
Puccinia species in cereals,
Rhizoctonia solani in cotton and lawns,
Ustilago species in cereals and sugar cane,
Venturia inaequalis (scab) in apples,
Septoria nodorum in wheat,
Pyrenophora teres in barley,
Botrytis cinerea (gray mold) in strawberries and vines,
Cercospora arachidicola in groundnuts,
Pseudocercosporella herpotrichoides in wheat and barley,
Pyricularia oryzae in rice,
Phytophthora infestans in potatoes and tomatoes,
Alternaria solani in potatoes and tomatoes,
Plasmopara viticola in grapes, and
Fusarium and
Verticillium species in various plants.

The compounds are applied by spraying or dusting plants with the active ingredients, or treating the seeds of the plants with the active ingredients. They are applied before or after infection of the plants or seeds by the fungi.

The novel substances can be converted to the conventional formulations, such as solutions, emulsions, suspensions, dusts, powders, pastes and granules. The application forms depend entirely on the purposes for which they are intended; they should at all events ensure a fine and uniform distribution of the active substance. The formulations are produced in a known manner, for example by extending the active ingredient with solvents and/or carriers, with or without the use of emulsifiers and dispersants; if water is used as a diluent, it is also possible to employ other, organic solvents as auxiliary solvents. Suitable assistants for this purpose are essentially solvents, such as aromatics (e.g. xylene or benzene), chlorinated aromatics (e.g. chlorobenzenes), paraffins (e.g. oil fractions), alcohols (e.g. methanol or butanol), ketones (e.g. cyclohexanone), amines (e.g. ethanolamine or dimethylformamide) and water; carriers, such as ground natural minerals (kaolins, aluminas, talc or chalk) and ground synthetic minerals (e.g. highly disperse silica or silicates); emulsifiers, such as nonionic and anionic emulsifiers (e.g. polyoxyethylene fatty alcohol ethers, alkylsulfonates and arylsulfonates) and dispersants, such as lignin, sulfite waste liquors and methylcellulose.

The fungicides generally contain from 0.1 to 95, preferably from 0.5 to 90, % by weight of active ingredient. The application rates are from 0.05 to 3 kg or more of active ingredient per ha, depending on the type of effect desired.

The novel compounds may also be employed in material protection, inter alia for controlling wood-destroying fungi, such as Coniophora puteana and Polystictus versicolor. The novel active ingredients can also be used as fungicidal components of oily wood preservatives for protecting wood against wood-discoloring fungi. They are used by treating, for example impregnating or painting, the wood with these agents.

Some of the novel compounds are extremely effective against human-pathogenic fungi, such as Trichophyton mentagrophytes and Candida albicans. The agents and the ready-to use formulations prepared from them, such as solution, emulsions, suspensions, powders, dusts, pastes or granules, are applied in a conventional manner, for example by spraying, atomizing, dusting scattering, dressing or watering.

Examples of such formulations are:

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 3 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 3 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 2 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 2 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts of compound no. 3 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

In these application forms, the agents according to the invention may also be present together with other active ingredients, for example herbicides, insecticides, growth regulators and fungicides, or may furthermore be mixed with fertilizers and applied together with these. Mixing with fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[bis-(dimethylamino)-phosphinyl]-3-phenyl-1,2,4-triazole,
2,3-dicyano-1,4-dithiaanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiin,
2,3-dihydro-5-carboxanilido-6-methyl-1,4-oxathiin 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-dimethylfuran-3-carboxamide, 2-methylbenzanilide,
2-iodobenzanilide,
N-formyl-N-morpholine-2,2,2-trichloroethylacetal, piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)butan-2-one,
1-(4-chlorophenoxy)-3,3-dimethyl-1-(1H-1,2,4-triazol-1-yl)butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

For the following experiments, the prior art active ingredients N-tridecyl-2,6-dimethylmorpholine (A) and its acetate (B) were used for comparison.

USE EXAMPLE 1

Action on powdery mildew of wheat

Leaves of pot-grown wheat seedlings of the Frühgold variety were sprayed with aqueous spray liquor containing (dry basis) 80% of active ingredient and 20% of emulsifier, and, 24 hours after the spray coating had dried on, the leaves were dusted with oidia (spores) of powdery mildew of wheat (*Erysiphe graminis* var. tritici). The test plants were then placed in a greenhouse at from 20° to 22° C. and from 75 to 80% relative humidity. After 7 days, the extent of powdery mildew spread was determined.

The results show that, when used as a liquor containing the active ingredient in a concentration of 0.025 and 0.0125 wt %, compounds 1 and 2 had a better fungicidal action (90%) than prior art compounds A and B (70%).

USE EXAMPLE 2

Action on wheat brown rust

Leaves of pot-grown wheat seedlings of the Frühgold variety were dusted with spores of brown rust (*Puccinia recondita*). The pots were then placed in a chamber at from 20° to 22° C. and with a high humidity (90-95%) for 24 hours. During this time, the spores germinated, and the germ tubes penetrated into the leaf tissue. The infected plants were then sprayed to runoff with aqueous spray liquors containing (dry basis) 80% of active ingredient and 20% of emulsifier. When the spray coating had dried on, the test plants were placed in a greenhouse at from 20° to 22° C. and from 65 to 70% relative humidity. After 8 days the extent of development of rust fungi on the leaves was determined.

The results show that, when used as a liquor containing the active ingredient in a concentration of 0.025%, for example compounds 1 and 2 had a good fungicidal action (97%).

USE EXAMPLE 3

Action on *Septoria nodorum*

Leaves of pot-grown wheat seedlings of the "Jubilar" variety were sprayed to runoff with aqueous spray liquors consisting (dry basis) of 80% of active ingredient and 20% of emulsifier. On the following day, the plants (with the dried-on layer) were infected with an aqueous spore suspension of Septoria nodorum, and then cultivated for a further 10 days at 17° to 19° C. and a relative humidity of 95%. The extent of fungus attack was then assessed visually.

The results of this experiment show that, when used as a liquor containing the active ingredient in an amount of 0.05%, for instance compounds 1 and 2 had a good fungicidal action (97%).

USE EXAMPLE 4

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results of the experiment show that for instance compounds 1, 2 and 3, applied as 0.05 and 0.125% spray liquors, had a good fungicidal action (97%).

We claim:

1. An acrylate of the formula

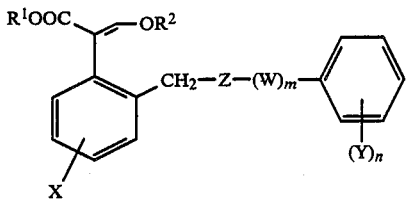

wherein $R^1$ and $R^2$ independently of one another are each $C_1$–$C_8$-alkyl, X is hydrogen, halogen, $C_1$–$C_4$-alkoxy, trifluoromethyl, cyano or nitro, W is unsubstituted or alkyl-substituted, saturated or unsaturated alkylene of up to 10 carbon atoms, Y is hydrogen, alkyl, trifluoromethyl, alkoxyalkyl, cycloalkyl, benzyl, phenyl, phenoxy, halogen, an unsubstituted $C_4H_4$ chain which is fused to the benzene radical to form a naphthyl ring, alkoxy, 1,1,2,2-tetrafluoroethoxy, thiocyanato, cyano, $NO_2$,

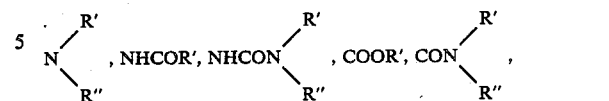

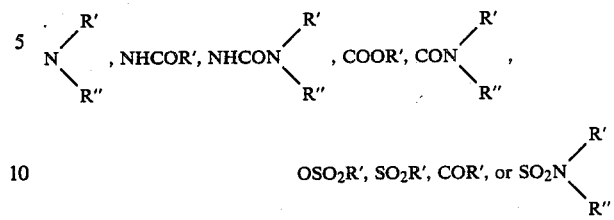

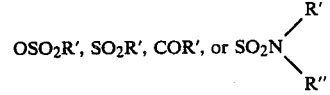

where R' and R" independently of one another are each hydrogen, alkyl, or cycloalkyl, or are phenyl which is unsubstituted or substituted by alkyl, halogen or alkoxy, m is 0 or 1, n is from 1 to 3 and Z is oxygen, sulfur, SO or $SO_2$.

2. A fungicide containing a carrier and a fungicidally effective amount of a compound as set forth in claim 1.

3. A process for combating fungi, wherein the fungi or the materials, plants, seeds or soil threatened by fungus attack are treated with a fungicidally effective amount of a compound as set forth in claim 1.

4. Methyl alpha-(2-phenoxymethylphenyl)-beta-methoxyacrylate.

5. A fungicide containing a carrier and a fungicidally effective amount of the compound set forth in claim 4.

* * * * *